US008859819B2

(12) United States Patent
Poigny

(10) Patent No.: US 8,859,819 B2
(45) Date of Patent: Oct. 14, 2014

(54) SULPHURATED DERIVATIVES OF RESORCINOL, PREPARATION OF SAME AND COSMETIC USES THEREOF

(75) Inventor: Stéphane Poigny, Saubens (FR)

(73) Assignee: Pierre Fabre Dermo-Cosmetique, Boulogne-Billancourt (FR)

( * ) Notice: Subject to any disclaimer, the term of this patent is extended or adjusted under 35 U.S.C. 154(b) by 307 days.

(21) Appl. No.: 13/263,347

(22) PCT Filed: Apr. 8, 2010

(86) PCT No.: PCT/EP2010/054619
§ 371 (c)(1),
(2), (4) Date: Oct. 7, 2011

(87) PCT Pub. No.: WO2010/115945
PCT Pub. Date: Oct. 14, 2010

(65) Prior Publication Data
US 2012/0034176 A1 Feb. 9, 2012

(30) Foreign Application Priority Data

Apr. 8, 2009 (FR) ...................................... 09 52289

(51) Int. Cl.
| C07C 323/20 | (2006.01) |
| C07C 321/24 | (2006.01) |
| A01N 37/10 | (2006.01) |
| A61Q 19/02 | (2006.01) |
| A61Q 19/08 | (2006.01) |
| A01N 41/10 | (2006.01) |
| A01N 47/10 | (2006.01) |
| A01N 31/16 | (2006.01) |
| C07C 317/22 | (2006.01) |
| A61Q 5/08 | (2006.01) |
| A61K 8/46 | (2006.01) |

(52) U.S. Cl.
CPC .............. *C07C 323/20* (2013.01); *A01N 37/10* (2013.01); *A61Q 19/02* (2013.01); *A61Q 19/08* (2013.01); *A01N 41/10* (2013.01); *A61K 2800/524* (2013.01); *A01N 47/10* (2013.01); *A01N 31/16* (2013.01); *C07C 317/22* (2013.01); *A61Q 5/08* (2013.01); *A61K 2800/522* (2013.01); *A61K 8/46* (2013.01)
USPC ............. 568/48; 568/708; 568/709; 568/712; 514/706; 514/708; 514/709; 514/712; 424/62

(58) Field of Classification Search
CPC .... C07C 317/14; C07C 317/16; C07C 317/24
See application file for complete search history.

(56) References Cited

U.S. PATENT DOCUMENTS

| 2,661,376 A | 12/1953 | Comer et al. |
| 4,275,240 A * | 6/1981 | Yamaguchi et al. ............. 568/37 |
| 4,287,366 A * | 9/1981 | Yamaguchi et al. ............. 568/33 |
| 4,555,469 A * | 11/1985 | Erdmann et al. ............... 430/168 |
| 6,610,890 B1 * | 8/2003 | Garcia de Quesada Fort et al. ................................ 568/332 |
| 7,119,159 B2 * | 10/2006 | Fehn et al. ....................... 528/15 |

FOREIGN PATENT DOCUMENTS

| EP | 0623341 A1 | 11/1994 | |
| GB | 855572 | * 12/1960 | |
| GB | 1277186 | * 7/1972 | ............. C07C 43/22 |
| JP | 64-46746 A | 2/1989 | |
| JP | H01237191 | * 9/1989 | ............... B41M 5/18 |
| JP | 5-213857 A | 8/1993 | |
| JP | 7-181648 A | 7/1995 | |
| JP | 2000168239 | * 6/2000 | ............... B41M 5/30 |
| JP | 2001260541 | * 9/2001 | ............... B41M 5/30 |
| JP | 2004066621 | * 3/2004 | ............... B41M 5/30 |
| WO | WO 9707790 | * 3/1997 | ............. A61K 31/12 |

OTHER PUBLICATIONS

JP 05-2138457, Kitayama et al, Melanine inhibitor, 1993, English translation. 10 pages.*
JP H01237191, Tsuji et al., Thermal recording material containing 4-hydroxydiphenyl sulfone compounds, 1989, English abstract. 1 page.*
JP 2000168239, Takahashi et al., Thermal recording material, 2000, English translation, 27 pages.*
JP 2001260541, Hata, et al., Heat sentative recording body, 2001, English translation, 7 pages.*
JP 2004066621, Fujii, et al., Recording member and recording sheet, 2004, English translation, 16 pages.*
McCullough et al., Preventon and treatment of skin aging, 2006, Annals of the New York Academy of Science, vol. 1067, issue 1, pp. 323-331.*

(Continued)

*Primary Examiner* — Yate K Cutliff
(74) *Attorney, Agent, or Firm* — Birch, Stewart, Kolasch & Birch, LLP

(57) ABSTRACT

The present invention relates to a compound of the general formula (I) where: X=S, SO or $SO_2$; and one of the radicals $R_1$ and $R_2$ is a hydrogen atom and the other is a radical: a $C_1$ to $C_{18}$ linear or branched alkyl, optionally substituted by one or more halogen atom(s); a $C_2$ to $C_{18}$ linear or branched alkenyl, optionally substituted by one or more halogen atom(s); an aralkyl, optionally substituted by one or more $C_1$ to $C_6$ alkoxy group(s); or a $COR_3$ or $CONHR_3$, but not simultaneously, where $R_3$ is a radical: a $C_1$ to $C_{18}$ linear or branched alkyl, optionally substituted by one or more halogen atom(s); a $C_2$ to $C_{18}$ linear or branched alkenyl, optionally substituted by one or more halogen atom(s); an aralkyl, optionally substituted by one or more $C_1$ to $C_6$ alkoxy group(s); an aralkenyl, optionally substituted by one or more $C_1$ to $C_6$ alkoxy groups and/or one or more OH group(s); or an aryl radical, optionally substituted by one or more $C_1$ to $C_6$ alkoxy group(s).

17 Claims, No Drawings

(56) References Cited

OTHER PUBLICATIONS

Hughes, et al., Sunscreent and prevention of skin aging, 2013, Annals of Internal Medicine, vol. 158, No. 11, pp. 781-790.*

Akai et al., "Total Synthesis of (±)-γ-Rubromycin on the Basis of Two Aromatic Pummerer-Type Reaction," Angewandte Chemie International Edition, vol. 46, 2007, pp. 7458-7461, XP002548108.

Dunning et al., "Preparation and Bacteriological Study of Some Symmetrical Organic Sulfides," Medicinal Chemistry, No. 53, Sep. 5, 1931, pp. 3466-3469, XP002548107.

Notification of Transmittal of the International Search Report and the Written Opinion of the International Searching Authority and International Search Report issued on May 12, 2010 for International Application No. PCT/EP2010/054619 (Forms PCT/ISA/220, PCT/ISA/210 and PCT/ISA/237).

* cited by examiner

SULPHURATED DERIVATIVES OF RESORCINOL, PREPARATION OF SAME AND COSMETIC USES THEREOF

The present invention relates to novel analogues of resorcinol sulphide, resorcinol sulphoxide and resorcinol sulphone corresponding to the generic formula (I):

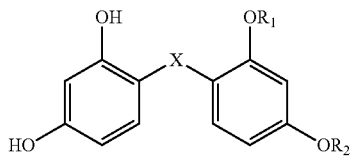

in which:
X=S, SO or $SO_2$, and;
one of the radicals $R_1$ and $R_2$ represents a hydrogen atom and the other a radical:
  a $C_1$ to $C_{18}$ linear or branched alkyl, optionally substituted by one or more halogen atom(s),
  a $C_2$ to $C_{18}$ linear or branched alkenyl, in particular an allyl group, or a 3,3 dimethylallyl group, or a geranyl group or a farnesyl group, optionally substituted by one or more halogen atom(s),
  an aralkyl, in particular benzyl, optionally substituted by one or more $C_1$ to $C_6$ alkoxy group(s), or
  $COR_3$ or $CONHR_3$, but not simultaneously, where $R_3$ represents a radical:
    a $C_1$ to $C_H$ linear or branched alkyl, optionally substituted by one or more halogen atom(s),
    a $C_2$ to $C_{18}$ linear or branched alkenyl, optionally substituted by one or more halogen atom(s),
    an aralkyl, in particular benzyl, optionally substituted by one or more $C_1$ to $C_6$ alkoxy group(s),
    an aralkenyl, optionally substituted by one or more $C_1$ to $C_6$ alkoxy group(s), and/or OH group(s), or instead
    an aryl radical, in particular phenyl, optionally substituted by one or more $C_1$ to $C_6$ alkoxy group(s).

The term "alkyl" represents linear or branched saturated aliphatic hydrocarbon chains and comprising the specified number of carbon atoms.

The term "alkenyl" represents linear or branched unsaturated aliphatic hydrocarbon chains and comprising the specified number of carbon atoms, for example an allyl group or a 3,3 dimethylallyl group or a geranyl group or a farnesyl group.

The term "alkoxy" represents a linear or branched hydrocarbon chain comprising the specified number of carbon atoms and an oxygen atom, for example a methoxy group, or an ethoxy group, or a propoxy group or a butoxy group.

The term "aryl" represents any monocyclic or bicyclic aromatic carbon ring, such as for example phenyl or naphthyl.

The term "aralkyl" designates an aryl bonded by an alkyl, for example a benzyl, ethylphenyl, propylphenyl.

The term "aralkenyl" designates an aryl bonded by an alkenyl, for example a phenyl acrylate or (4-methoxyphenyl)acrylate or (3, 4-dimethoxyphenyl)acrylate.

The term "halogen" represents fluorine, chlorine, bromine or iodine.

The term "oleoyl" represents the univalent radical derived from oleic acid by the loss of the OH group.

The term "linoleoyl" represents the univalent radical derived from linoleic acid by the loss of the OH group.

The term "alpha-linolenoyl" represents the univalent radical derived from alpha-linolenic acid by the loss of the OH group.

The term "gamma-linolenoyl" represents the univalent radical derived from gamma-linolenic acid by the loss of the OH group.

The term "coumaroyl" represents 4-hydroxycinnamoyl.

The term "caffeoyl" represents 3,4-dihydroxycinnamoyl.

The term "feruoyl" represents 4-hydroxy-3-methoxycinnamoyl.

The term "sinapoyl" represents 4-hydroxy-3,5-dimethoxycinnamoyl.

Among the compounds of generic formula (I) belonging to the present invention, a particularly appreciated class of compounds corresponds to compounds of generic formula (I) in which X=S. Similarly, the present invention particularly relates to compounds of generic formula (I) in which X=S and $R_2$=H.

In a preferred manner, the compounds according to the invention correspond to compounds of formula (I) in which X=S, $R_2$=H and $R_1$ is selected from the group consisting in:
  a $C_1$ to $C_{18}$ linear or branched alkyl or a $C_2$ to $C_{18}$ linear or branched alkenyl or $COR_3$ and $CONHR_3$.

According to an embodiment of the present invention, the compounds of generic formula (I) are those for which $R_1$ represents:
  a $C_1$ to $C_8$ linear or branched alkyl and in particular $C_4$ to $C_8$; or
  a $C_2$ to $C_{18}$ linear or branched alkenyl chosen from an allyl group or a 3,3 dimethylallyl group or a geranyl group or a farnesyl group; or
  a benzyl.

According to the invention, a particularly appreciated class of compounds of generic formula (I) corresponds to compounds for which $R_3$ represents:
  a $C_7$ to $C_{15}$ linear or branched alkyl and in particular $C_{11}$ to $C_{15}$; or
  a $C_{10}$ to $C_{18}$ linear or branched alkenyl, or
  a benzyl; or
  an aralkenyl chosen from phenyl acrylate or (4-methoxyphenyl)acrylate or (3,4-dimethoxyphenyl)acrylate; or
  a phenyl.

According to a specific embodiment of the invention, the compounds of generic formula (I) are those in which $COR_3$ represents:
  an oleoyl or a linoleoyl or an alpha-linolenoyl or a gamma-linolenoyl.

According to another specific embodiment of the invention, the compounds of formula (I) are those for which $COR_3$ represents:
  a cinnamoyl substituted by one or more $C_1$ to $C_6$ alkoxy group(s) and/or OH group(s) chosen from coumaroyl or 4-methoxycinnamoyl or 3,4-dimethoxycinnamoyl or caffeoyl or feruoyl or sinapoyl.

According to an embodiment of the invention, the compounds of generic formula (I) may be chosen from the following compounds:
4-(4-hydroxy-2-((2E,6E)-3,6,11-trimethyldodeca-2,6,10-5 trienyloxy)phenylthio)benzene-1,3-diol,
4-(4-hydroxy-2-(3-methylbut-2-enyloxy)phenylthio)benzene-1,3-diol,
(E)-4-(2-(3,7-dimethylocta-2,6-dienyloxy)-4-hydroxyphenylthio)benzene-1,3-diol,
4-(2-butoxy-4-hydroxyphenylthio)benzene-1,3-diol,
4-(4-butoxy-2-hydroxyphenylthio)benzene-1,3-diol,
4-(4-hydroxy-2-(octyloxy)phenylthio)benzene-1,3-diol,
4-(2-hydroxy-4-(octyloxy)phenylthio)benzene-1,3-diol, 4-(2-(benzyloxy)-4-hydroxyphenylthio)benzene-1,3-diol,
4-(4-(benzyloxy)-2-hydroxyphenylthio)benzene-1,3-diol,
4-(4-hydroxy-2-(4-methoxybenzyloxy)phenylthio)benzene-1,3-diol,
4-(2-(decyloxy)-4-hydroxyphenylthio)benzene-1,3-diol,
4-(2-(hexadecyloxy)-4-hydroxyphenylthio)benzene-1,3-diol,
2-(2,4-dihydroxyphenylthio)-5-hydroxyphenyldodecanoate,
2-(2,4-dihydroxyphenylthio)-5-hydroxyphenylpalmitate,
2-(2,4-dihydroxyphenylthio)-5-hydroxyphenyloctanoate,
4-(2,4-dihydroxyphenylthio)-3-hydroxyphenyloctanoate,
2-(2,4-dihydroxyphenylthio)-5-hydroxyphenyl3-phenylpropanoate,
4-(2,4-dihydroxyphenylthio)-3-hydroxyphenyl3-phenylpropanoate,
2-(2,4-dihydroxyphenylthio)-5-hydroxyphenyl3-methylbutanoate,
4-(2,4-dihydroxyphenylthio)-3-hydroxyphenyl3-methylbutanoate,
(9Z, 12Z)-2-(2,4-dihydroxyphenylthio)-5-hydroxyphenyl octadeca-9,12-dienoate
(E)-2-(2,4-dihydroxyphenylthio)-5-hydroxyphenyl3-(4-methoxyphenyl)acrylate,
(E)-2-(2,4-dihydroxyphenylthio)-5-hydroxyphenyl3-(3,4-dimethoxyphenyl)acrylate,
2-(2,4-dihydroxyphenylthio)-5-hydroxyphenyloctylcarbamate,
2-(2,4-dihydroxyphenylsulphinyl)-5-hydroxyphenyldodecanoate,
(9Z,12Z)-2-(2,4-dihydroxyphenylsulphinyl)-5-hydroxyphenyl octadeca-9,12-dienoate
4-(2-(decyloxy)-4-hydroxyphenylsulphinyl)benzene-1,3-diol,
4-(2-(decyloxy)-4-hydroxyphenylsulphonyl)benzene-1,3-diol, The invention also relates to the cosmetic use of compounds of formula (I'), which include, in addition novel analogues of formula (I), resorcinol sulphide, resorcinol sulphoxide and resorcinol sulphone, and in particular their use for the depigmentation of the skin, for the implementation of a method of cosmetic treatment of skin ageing. Generic formula (I'):

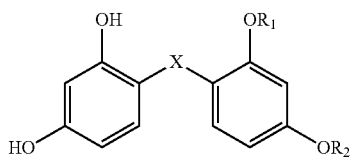

(I')

in which the radicals X, $R_1$ and $R_2$ have significations identical to those given with regard to formula (I), but where $R_1$ and $R_2$ can also represent simultaneously a hydrogen atom.

The present invention relates to the cosmetic use of compounds of generic formula (I') or formula (I) as antioxidant active ingredient or as depigmenting active ingredient.

The subject matter of the present invention is also the use of compounds of generic formula (I) as medicine and in particular as antibacterial active ingredient.

The invention also relates to pharmaceutical or cosmetic compositions comprising at least one of the compounds of formula (I) or formula (I') in association with at least one pharmaceutically or cosmetically acceptable excipient.

In the present invention, "pharmaceutically or cosmetically acceptable" is taken to designate that which is useful in the preparation of a pharmaceutical or cosmetic composition, which is generally safe, non toxic and neither biologically or otherwise undesirable and which is acceptable for therapeutic or cosmetic use, particularly by topical application.

The subject matter of the invention relates to a cosmetic composition characterised in that the quantity of compound of formula (I) or formula (I') varies between 0.01% and 10% and preferably from 0.1% to 5% by weight with respect to the total weight of the composition.

The present invention relates to a method of bleaching and/or lightening of the human skin and/or body hair and/or head hair comprising the application on the skin and/or body hair and/or head hair of a cosmetic composition containing at least one compound of formula (I) or formula (I').

The present invention relates to a method of cosmetic treatment and/or prevention of the ageing of the skin comprising the application on the skin of a cosmetic composition containing at least one compound of formula (I) or formula (I')

The subject matter of the invention also extends to the method of synthesising novel compounds of formula (I).

According to another characteristic of the present invention, it also relates to a method of preparing a compound of generic formula (I) characterised in that 4,4'-thiodibenzene-1,3-diol or 4,4'-sulphinylbis-1,3-benzenediol is made to react with a halide of formula II:

(II)

in which:

Hal represents a halogen atom, and $R_1$ has the same signification as that given previously regarding formula (I) with the exception of a hydrogen atom.

According to another characteristic of the present invention, it also relates to a method of preparing a derivative of resorcinol of formula (I) in which X represents SO or $SO_2$, characterised in that a compound of formula (I), in which X represents a sulphur atom, is oxidised in particular by means of an aqueous solution of hydrogen peroxide.

The present invention will be better understood with respect to the examples given hereafter for purely illustrative purposes.

I. SYNTHESIS OF COMPOUNDS OF THE INVENTION

1) Synthesis of Analogues of Resorcinol Sulphide

Example 1 (Resorcinol Sulphide)

4,4'-thiodibenzene-1,3-diol

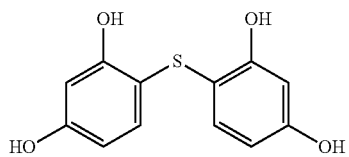 [SMILES: Oc1ccc(Sc2ccc(O)cc2O)c(O)c1]

$^1$H NMR (400 MHz, DMSO-d6): δ: 6.19 (dd, 2H); 6.34 (d, 2H); 6.87 (d, 2H); 9.41 (wide s, 2H); 9.50 (wide s, 2H).

$^{13}$C NMR (100 MHz, DMSO d6): δ: 102.58; 107.52; 111.46; 133.90; 157.04; 158.37.

MS (ESI−): 249.1 [M−H]−

A) Synthesis of Ethers: Synthesis of Ethers by Coupling of Resorcinol Sulphide with an Alkyl Halide.

To a suspension of 4,4'-thiodibenzene-1,3-diol (resorcinol sulphide, 3 g, 12 mmol, 4 eq.) and potassium carbonate (497 mg, 3.6 mmol, 1.2 eq.) in 20 ml of anhydrous DMF (=dimethylformamide) and under nitrogen, are added 856 mg of farnesyl bromide (3 mmol, 1 eq.) then the mixture is stirred at 80° C. for 6 hours. The reaction is followed by TLC (=thin layer chromatography).

After returning to room temperature, the solvent is evaporated then the residue is extracted with an ethyl acetate/water mixture. The organic phase is washed twice with water then with a saturated NaCl solution. After drying over magnesium sulphate, a solid is obtained after evaporation of the solvent. The solid is washed with DCM (=dichloromethane) then collected to provided 2 g of starting resorcinol sulphide that has not reacted.

The filtrate (DCM) is then evaporated to lead to an oil purified on silica by a heptane/ethyl acetate mixture (95/5 to 50/50) or by preparative HPLC. The product obtained in the form of a colourless oil is dried under vacuum overnight. 730 mg are then obtained with a yield of 55%.

The structure is determined by proton NMR, carbon NMR, HMBC, HMQC and NOESY analyses.

Example 2

4-(4-hydroxy-2-((2E,6E)-3,6,11-trimethyldodeca-2,6,10-trienyloxy)phenylthio)benzene-1,3-diol

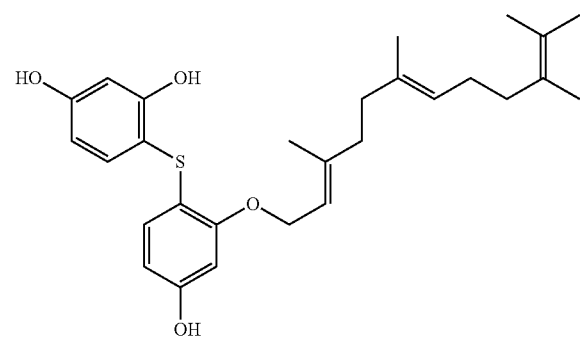 [SMILES: CC(C)=C(C)CC/C=C(\C)CC/C(C)=C/COc1cc(O)ccc1Sc1ccc(O)cc1O]

$^1$H NMR (500 MHz, CDCl$_3$): δ: 1.58 (s, 3H); 1.60 (s, 3H); 1.66 (s, 3H); 1.73 (s, 3H); 1.96 (m, 2H); 2.04 (m, 2H); 2.09 (m, 2H); 2.14 (m, 2H); 4.56 (d, j=6.4 Hz, 2H); 5.01 (s, 1H, OH para S); 5.06 (s, 1H, OH para S); 5.07 (m, 1H); 5.11 (m, 1H); 5.51 (t, 1H); 6.29 (d, j=8.5-2.4 Hz, 1H); 6.32 (d, j=8.2-2.7 Hz, 1H); 6.38 (d, j=2.4 Hz, 1H); 6.42 (d, j=2.7 Hz, 1H); 7.08 (d, j=8.5 Hz, 1H); 7.33 (s, 1H, OH ortho S); 7.38 (d, j=8.5 Hz, 1H).

$^{13}$C NMR (125 MHz, CDCl$_3$): δ: 16.04; 16.75; 17.69; 25.70; 26.20; 26.70; 39.54; 15 39.66; 65.99; 100.68; 102.31; 108.18; 108.33; 110.79; 115.32; 118.49; 123.62; 124.34; 131.38; 133.99; 135.50; 137.54; 142.24; 156.88; 158.09; 158.48; 158.73.

MS (APCI): 455.2 [M+H]$^+$

Rf (1/1; Heptane/EtOAc): 0.75

Example 3

4-(4-hydroxy-2-(3-methylbut-2-enyloxy)phenylthio)benzene-1,3-diol

From 1-bromo-3-methylbut-2-ene (=alkyl halide)

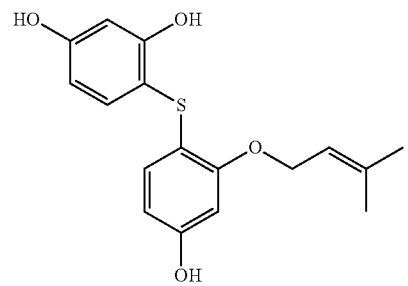 [SMILES: CC(C)=CCOc1cc(O)ccc1Sc1ccc(O)cc1O]

$^1$H NMR (400 MHz, CDCl$_3$): δ: 1.76 (s, 3H); 1.82 (s, 3H); 4.56 (d, 2H); 5.07 (m, 2H, 2×OH para S); 5.53 (t, 1H); 6.30-6.45 (m, 4H); 7.09 (d, 1H); 7.32 (s, 1H); 7.40 (d, 1H).
MS (APCI+): 319.0 [M+H]$^+$ Example 4

(E)-4-(2-(3,7-dimethylocta-2,6-dienyloxy)-4-hydroxy phenylthio)benzene-1,3-diol

From geranyl chloride

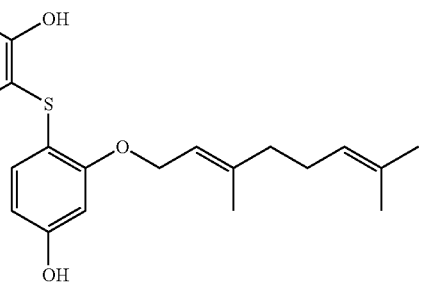

$^1$H NMR (400 MHz, CDCl$_3$): δ: 1.62 (s, 3H); 1.68 (s, 3H); 1.75 (s, 3H); 2.13 (m, 2H); 4.59 (d, 2H); 4.80 (s, 1H); 4.85 (s, 1H); 5.11 (s, 1H); 5.53 (t, 1H); 6.30-6.45 15 (m, 4H); 7.09 (d, 1H); 7.32 (s, 1H); 7.41 (d, 1H).
MS (APCI+): 386.9 [M+H]$^+$

Example 5

4-(2-butoxy-4-hydroxyphenylthio)benzene-1,3-diol

From 1-bromo-butane. Majority product (590 mg)

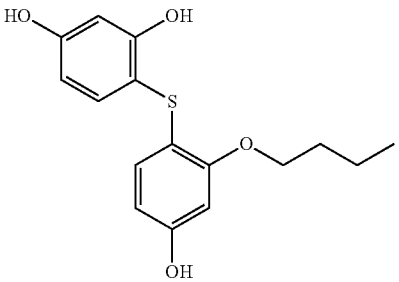 [SMILES: CCCCOc1cc(O)ccc1Sc1ccc(O)cc1O]

$^1$H NMR (400 MHz, CDCl$_3$): δ: 1.01 (t, 3H); 1.53 (m, 2H); 1.88 (m, 2H); 4.02 (t, 2H); 4.78 (wide s, 2H, 2 OH para S); 6.32 (m, 2H); 6.36 (s, 1H); 6.45 (s, 1H); 7.08 (d, 1H); 7.29 (s, 1H, OH ortho S); 7.40 (d, 1H).
MS (APC1+): 307.0 [M+H]$^+$

Example 6

4-(4-butoxy-2-hydroxyphenylthio)benzene-1,3-diol

From 1-bromo-butane. Minority product (18 mg)

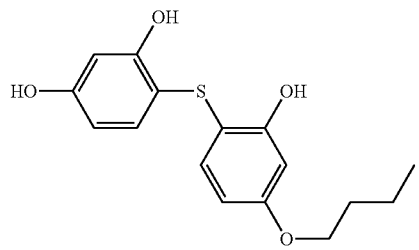 [SMILES: CCCCOc1ccc(Sc2ccc(O)cc2O)c(O)c1]

$^1$H NMR (400 MHz, CDCl$_3$): δ: 1.02 (t, 3H); 1.44 (m, 2H); 1.72 (m, 2H); 3.90 (t, 2H); 6.34 (d, 1H); 6.41 (d, 1H); 6.43 (s, 1H); 6.49 (s, 1H); 7.25 (m, 3H).
MS (APCI+): 307.1 [M+H]$^+$

Example 7

4-(4-hydroxy-2-(octyloxy)phenylthio)benzene-1,3-diol

From 1-bromo-octane. Majority product (1.3 g)

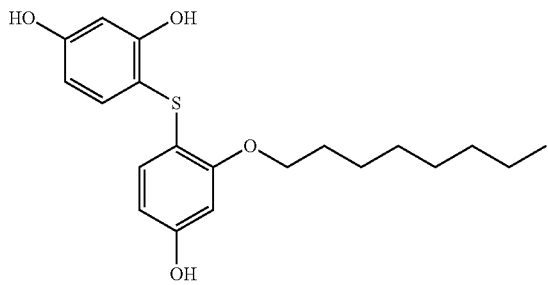 [SMILES: CCCCCCCCOc1cc(O)ccc1Sc1ccc(O)cc1O]

$^1$H NMR (400 MHz, CDCl$_3$): δ: 0.91 (t, 3H); 1.30 (m, 8H); 1.47 (m, 2H); 1.88 (m, 2H); 3.99 (t, 2H); 4.90 (wide s, 2H); 6.30 (d, 1H); 6.35 (d, 1H); 6.36 (s, 1H); 6.45 (s, 1H); 7.07 (d, 1H); 7.32 (wide s, 1H); 7.41 (d, 1H).
MS (APCI+): 363.2 [M+H]$^+$

Example 8

4-(2-hydroxy-4-(octyloxy)phenylthio)benzene-1,3-diol

From 1-bromo-octane. Minority product (100 mg)

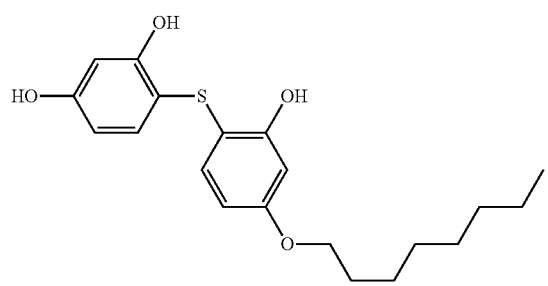 [SMILES: CCCCCCCCOc1ccc(Sc2ccc(O)cc2O)c(O)c1]

$^1$H NMR (400 MHz, CDCl$_3$): δ: 0.87 (t, 3H); 1.27 (m, 8H); 1.41 (m, 2H); 1.72 (m, 2H); 3.90 (t, 2H); 6.34 (d, 1H); 6.41 (d, 1H); 6.44 (s, 1H); 6.48 (s, 1H); 7.25 (m, 3H).
MS (APCI+): 363.1 [M+H]$^+$

Example 9

4-(2-(benzyloxy)-4-hydroxyphenylthio)benzene-1,3-diol

From benzyl bromide. Majority product (600 mg)

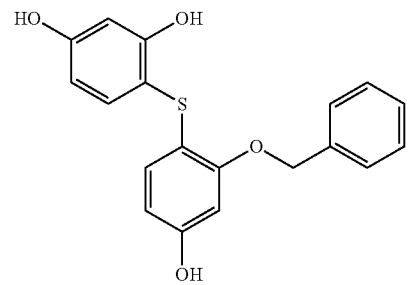 [SMILES: Oc1ccc(Sc2ccc(O)cc2OCc2ccccc2)c(O)c1]

$^1$H NMR (400 MHz, CDCl$_3$): δ: 4.80 (m wide, 2H); 5.14 (s, 2H); 6.34 (m, 2H); 6.44 (s, 2H); 7.02 (d, 1H); 7.08 (s, 1H); 7.34-7.41 (m, 6H).
MS (APCI+): 341.1 [M+H]$^+$

Example 10

4-(4-(benzyloxy)-2-hydroxyphenylthio)benzene-1,3-diol

From benzyl bromide. Minority product (28 mg)

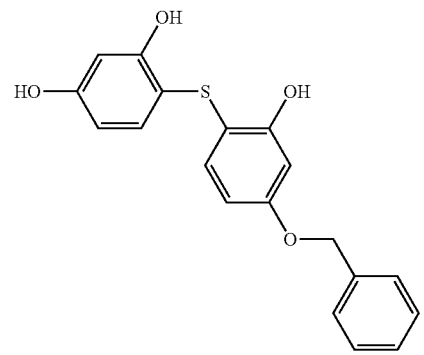 [SMILES: Oc1ccc(Sc2ccc(OCc3ccccc3)cc2O)c(O)c1]

$^1$H NMR (400 MHz, CDCl$_3$): δ: 5.00 (s, 2H); 6.34-6.57 (m, 4H); 7.28-7.39 (m, 7H).
MS (APCI+): 341.1 [M+H]$^+$

Example 11

4-(4-hydroxy-2-(4-methoxybenzyloxy)phenylthio)benzene-1,3-diol

From 4-methoxybenzyl bromide. Majority product (600 mg)

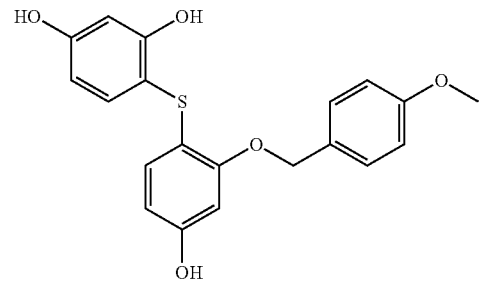 [SMILES: COc1ccc(COc2cc(O)ccc2Sc2ccc(O)cc2O)cc1]

$^1$H NMR (400 MHz, CDCl$_3$): δ: 3.82 (s, 3H); 5.04 (s, 2H); 5.24 (m wide, 2H); 6.34 (m, 2H); 6.44 (m, 2H); 6.92 (d, 2H); 7.03 (d, 1H); 7.14 (wide s, 1H); 7.37 (m, 3H).
MS (APCI+): 371.0 [M+H]$^+$

Example 12

4-(2-(decyloxy)-4-hydroxyphenylthio)benzene-1,3-diol

Procedure of example 2 but with 2 equivalents of resorcinol sulphide, 1 equivalent of 1-iododecane, 16 hours at room temperature. The product is obtained in the form of a white solid after purification with a yield of 83%.

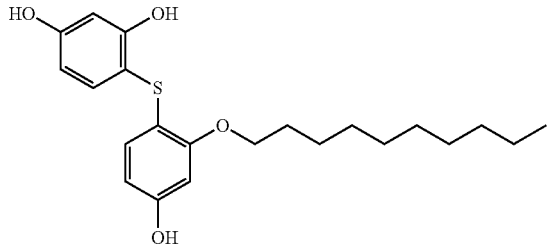 [SMILES: CCCCCCCCCCOc1cc(O)ccc1Sc1ccc(O)cc1O]

$^1$H NMR (400 MHz, CDCl$_3$): δ: 0.91 (t, 3H); 1.25 (m, 12H); 1.47 (m, 2H); 1.88 (m, 2H); 3.99 (t, 2H); 4.90 (wide s, 2H); 6.30 (d, 1H); 6.35 (d, 1H); 6.36 (s, 1H); 6.45 10 (s, 1H); 7.07 (d, 1H); 7.32 (wide s, 1H); 7.41 (d, 1H).
$^{13}$C NMR (100 MHz, DMSO): δ:13.89; 22.04; 25.39; 28.56; 28.65; 28.70; 28.89; 28.94; 31.24; 67.76; 100.18; 102,66; 107.47; 107.62; 107.98; 113.65; 130.42; 135.21; 156.83; 157.34; 158.20; 158.81
MS (APCI+): 391.1 [M+H]$^+$

Example 13

4-(2-(hexadecyloxy)-4-hydroxyphenylthio)benzene-1,3-diol

Same synthesis as SP02-131 from 1-iodo-hexadecane Product obtained in the form of a white solid with a yield of 84%.

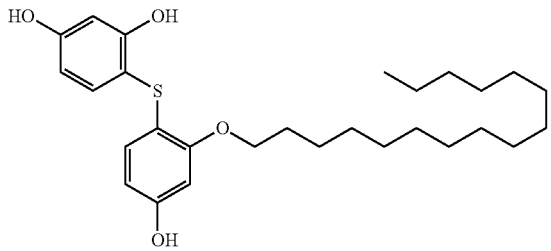 [SMILES: CCCCCCCCCCCCCCCCOc1cc(O)ccc1Sc1ccc(O)cc1O]

$^1$H NMR (400 MHz, CDCl$_3$): δ: 0.88 (t, 3H); 1.2 (m, 24H); 1.47 (m, 2H); 1.84 (m, 2H); 3.92 (t, 2H); 5.31 (wide s, 2H); 6.27 (dd, 1H); 6.33 (s, 1H); 6.36 (d, 1H); 6.45 (s, 1H); 7.05 (d, 1H); 7.38 (wide s, 1H); 7.41 (d, 1H).
$^{13}$C NMR (100 MHz, CDCl$_3$): δ: 14.11; 22.68; 25.95; 28.89; 29.35; 29.56; 29.61; 29.66; 29.70; 31,91; 69.22; 100.39; 102,29; 108.19; 108.54; 110.89; 115.01; 133.93; 137.49; 156.88; 158.19; 158.40; 158.44.
MS (ESI−): 473.2 [M−H]

B) Synthesis of Esters
a) Route 1: Coupling from Resorcinol Sulphide

To a solution of 4,4'-thiodibenzene-1,3-diol (resorcinol sulphide, 1 g, 4 mmol, 4 eq.) and triethylamine (177 μl, 1.2 mmol, 1.2 eq.) in 20 ml of anhydrous THF (tetrahydrofuran) and under nitrogen, are added drop by drop 219 mg of lauroyl chloride (1 mmol, 1 eq.) then the mixture is stirred at room temperature for 1 hour. The reaction is followed by TLC.

After returning to room temperature, the solvent is evaporated then the residue extracted with an ethyl acetate/water mixture. The organic phase is washed twice with water then with a saturated NaCl solution. After drying over magnesium sulphate, a solid is obtained after evaporation of the solvent. The solid is washed with DCM then collected to provide 510 mg of starting resorcinol sulphide that has not reacted.

The filtrate (DCM) is then evaporated to lead to an oil purified on silica by a cyclohexane/ethyl acetate mixture (9/1) or by preparative HPLC (high performance liquid chromatography). The product obtained in the form of a colourless oil is dried under vacuum overnight. The product solidifies when cold. 260 mg are then obtained in the form of a white solid with a yield of 60%.

Example 14

2-(2,4-dihydroxyphenylthio)-5-hydroxyphenyl dodecanoate

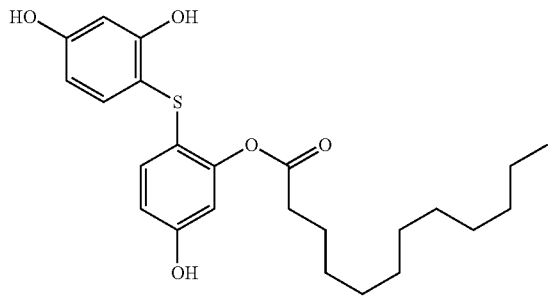 [SMILES: CCCCCCCCCCCC(=O)Oc1cc(O)ccc1Sc1ccc(O)cc1O]

$^1$H NMR (500 MHz, CDCl$_3$): δ: 0.86 (t, J=7 Hz, 3H); 1.32 (m, 17H); 1.79 (q, J=7.6 Hz, 2H); 2.63 (t, J=7.5 Hz, 2H); 5.30 (s, 1H); 5.35 (s, 1H); 6.38 (dd, J=8.4 and 2.6 Hz, 1H); 6.45 (d, J=2.7 Hz, 1H); 6.48 (dd, J=8.5 and 2.7 Hz, 1H); 6.50 (d, J=2.4 Hz, 1H); 6.73 (d, J=8.5 Hz, 1H); 6.76 (s, 1H); 7.35 (d, j=8.5 Hz, 1H).
$^{13}$(NMR (125 MHz, CDCl$_3$): δ: 14.12; 22.67; 24.83; 29.13; 29.22; 29.32; 29.44; 29.59; 31.89; 34.24; 103.01; 107.84; 108.72; 110.12; 114.67; 120.06; 130.45; 137.96; 148.93; 155.48; 158.48; 159.03; 172.98.
MS (APCI): 433.1 [M+H]$^+$
Rf (7/3; Heptane/EtOAc): 0.58

Example 15

2-(2,4-dihydroxyphenylthio)-5-hydroxyphenyl octanoate

From octanoyl chloride

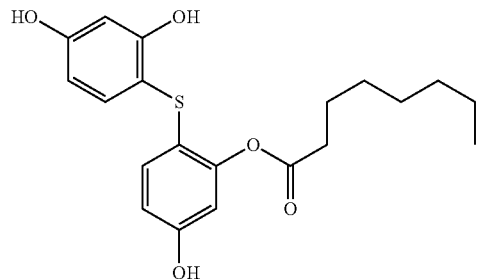 [SMILES: CCCCCCCC(=O)Oc1cc(O)ccc1Sc1ccc(O)cc1O]

$^1$H NMR (400 MHz, CDCl$_3$): δ: 0.82 (t, 3H); 1.29 (m, 8H); 1.63 (m, 2H); 2.35 (t, 2H); 6.41 (d, 1H); 6.49 (s, 1H); 6.56 (s, 1H); 6.57 (d, 1H); 6.81 (d, 1H); 7.39 (d, 20 1H).
MS (APCI+): 377.1 [M+H]$^+$

Example 16

4-(2,4-dihydroxyphenylthio)-3-hydroxyphenyl octanoate

From octanoyl chloride

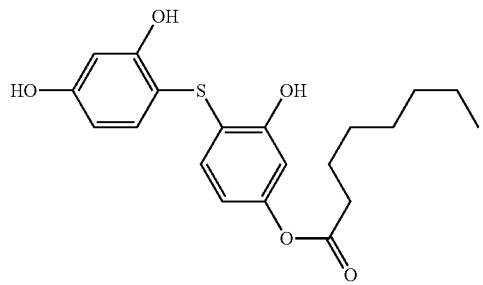 [SMILES: CCCCCCCC(=O)Oc1ccc(Sc2ccc(O)cc2O)c(O)c1]

$^1$H NMR (400 MHz, CDCl$_3$): δ: 0.88 (t, 3H); 1.33 (m, 8H); 1.72 (m, 2H); 2.3 (t, 2H); 6.36 (d, 1H); 6.41 (s, 1H); 6.58 (d, 1H); 6.71 (s, 1H); 7.31 (m, 2H). 5
MS (APCI+): 377.1 [M+H]$^+$

Example 17

2-(2,4-dihydroxyphenylthio)-5-hydroxyphenyl 3-phenylpropanoate

From hydro-cinnamoyl chloride

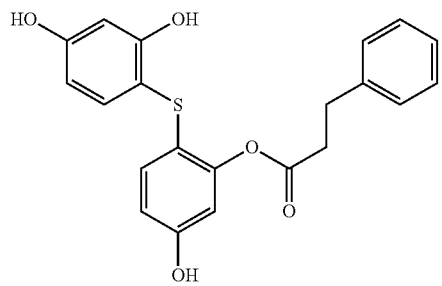 [SMILES: O=C(CCc1ccccc1)Oc1cc(O)ccc1Sc1ccc(O)cc1O]

$^1$H NMR (400 MHz, CDCl$_3$): δ: 2.98 (t syst AB, 2H); 3.13 (t syst AB, 2H); 5.40 (wide s, 2H); 6.41 (d, 1H); 6.46 (s, 1H); 6.48 (s, 1H); 6.54 (d, 1H); 6.79 (d, 1H); 7.22-7.38 (m, 6H).
MS (APCI+): 383.1 [M+H]$^+$

Example 18

4-(2,4-dihydroxyphenylthio)-3-hydroxyphenyl 3-phenylpropanoate

From hydro-cinnamoyl chloride

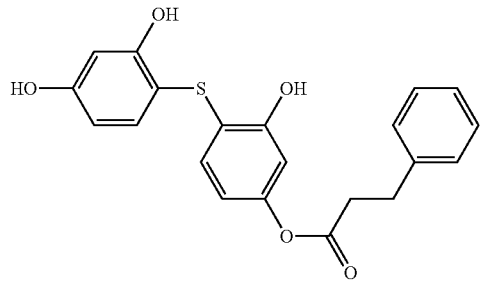 [SMILES: O=C(CCc1ccccc1)Oc1ccc(Sc2ccc(O)cc2O)c(O)c1]

$^1$H NMR (400 MHz, CDCl$_3$): δ: 2.86 (t syst AB, 2H); 3.04 (t syst AB, 2H); 6.36 (d, 1H); 6.42 (s, 1H); 6.50 (d, 1H); 6.61 (s, 1H); 7.22-7.38 (m, 7H).
MS (APCI+): 383.1 [M+H]$^+$

Example 19

2-(2,4-dihydroxyphenylthio)-5-hydroxyphenyl 3-methylbutanoate

From isovaleroyl chloride

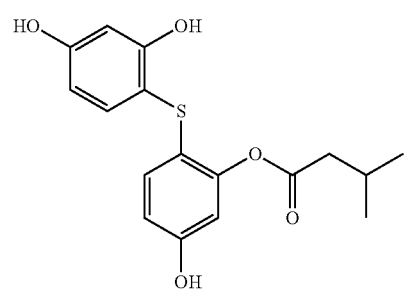 [SMILES: CC(C)CC(=O)Oc1cc(O)ccc1Sc1ccc(O)cc1O]

$^1$H NMR (400 MHz, CDCl$_3$): δ: 1.10 (d, 6H); 2.31 (m, 1H); 2.53 (d, 2H); 4.79 (wide s, 1H); 4.87 (wide s, 1H); 6.42 (d, 1H); 6.49 (s, 1H); 6.56 (s, 1H); 6.58 (d, 1H); 6.76 (s, 1H); 6.82 (d, 1H); 7.40 (d, 1H).
MS (APCI+): 335.0 [M+H]$^+$

Example 20

4-(2,4-dihydroxyphenylthio)-3-hydroxyphenyl 3-methylbutanoate

From isovaleroyl chloride

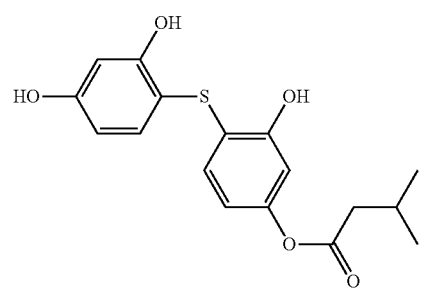 [SMILES: CC(C)CC(=O)Oc1ccc(Sc2ccc(O)cc2O)c(O)c1]

$^1$H NMR (400 MHz, CDCl$_3$): δ: 1.03 (d, 6H); 2.22 (m, 1H); 2.40 (d, 2H); 4.75 (wide s, 2H); 6.38 (d, 1H); 6.46 (s, 1H); 6.57 (d, 1H); 6.69 (s, 1H); 7.30 (m, 3H).
MS (APCI+): 335.1 [M+H]$^+$

Example 21

(9Z, 12Z)-2-(2,4-dihydroxyphenylthio)-5-hydroxyphenyl octadeca-9,12-dienoate

From linoleoyl chloride

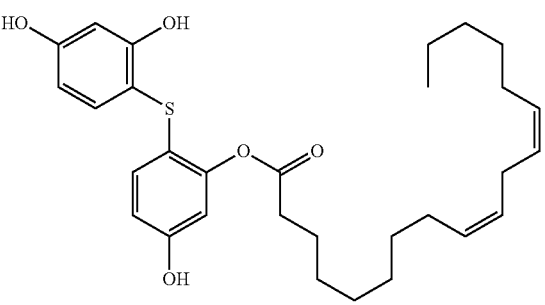 [SMILES: CCCCC/C=C\C/C=C\CCCCCCCC(=O)Oc1cc(O)ccc1Sc1ccc(O)cc1O]

$^1$H NMR (400 MHz, CDCl$_3$): δ: 0.88 (t, 3H); 1.32 (m, 14H); 1.80 (m, 2H); 2.04 (m, 4H); 2.63 (t, 2H); 2.79 (t, 2H); 5.35 (m, 4H); 6.38 (d, 1H); 6.45 (s, 1H); 6.51 (m, 2H); 6.73 (d, 1H); 7.35 (d, 1H).

MS (ESI): 513.2 [M+H]$^+$

Rf (1/1; Heptane/EtOAc): 0.75 b) Route 2: Coupling via Carbodiimide

To a solution of N-(3-Dimethylaminopropyl)-N'-ethylcarbodiimide hydrochloride (960 mg, 5 mmol) and 4-DMAP (4-dimethylaminopyridine) (0.5 mmol) in 20 ml of anhydrous DMF under N$_2$ are added 620 mg of 4-methoxycinnamic acid (3.5 mmol) then the mixture is stirred for 15 minutes. 3.5 g of 4,4'-thiodibenzene-1,3-diol (resorcinol sulphide, 14 mmol, 4 eq.) are added then the mixture is stirred at room temperature for 4 days.

The solvent is evaporated then the residue purified over silica CHCl$_3$/MeOH (95/5) to provide 320 mg of pure product in the form of a white solid after evaporation and drying in the vacuum oven. Yield: 22%

Example 22

(E)-2-(2,4-dihydroxyphenylthio)-5-hydroxyphenyl 3-(4-metoxyphenyl)acrylate

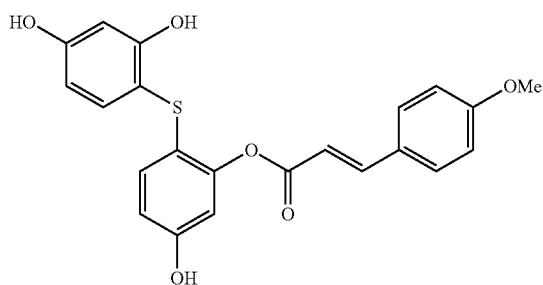 [SMILES: COc1ccc(/C=C/C(=O)Oc2cc(O)ccc2Sc2ccc(O)cc2O)cc1]

$^1$H NMR (400 MHz, CDCl$_3$): δ: 3.86 (s, 3H); 5.00 (wide s, 1H); 5.07 (wide s, 1H); 6.40 (dd, 1H); 6.48 (d, 1H); 6.60 (m, 2H); 6.64 (d, 1H); 6.85 (d, 1H); 6.95 (d, 2H); 7.40 (d, 1H); 7.58 (d, 2H); 7.91 (d, 1H).

MS (APCI+): 411.0 [M+H]$^+$

Rf (1/1; Heptane/EtOAc): 0.14

Example 23

(E)-2-(2,4-dihydroxyphenylthio)-5-hydroxyphenyl 3-(3,4-dimethoxyphenyl)acrylate

From 3,4-dimethoxycinnamic acid

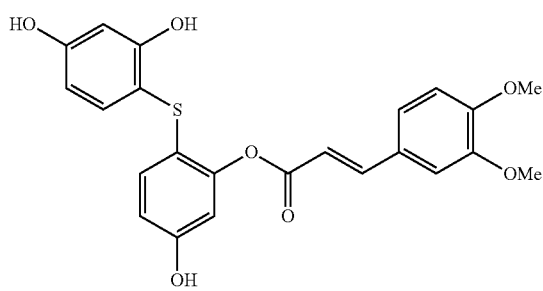 [SMILES: COc1ccc(/C=C/C(=O)Oc2cc(O)ccc2Sc2ccc(O)cc2O)cc1OC]

$^1$H NMR (400 MHz, DMSO-d6): δ: 3.82 (s, 3H); 3.84 (s, 3H); 6.22 (d, 1H); 6.37 (d, 1H); 6.61 (s, 1H); 6.64 (d, 1H); 6.77 (d, 1H); 6.92 (m, 2H); 7.01 (d, 1H); 7.31 (d, 1H); 7.43 (s, 1H); 7.72 (d, 1H); 9.58 (m, 2H); 9.78 (m, 1H).

MS (ESI+): 441.0 [M+H]$^+$

Rf (95/5; DCM/MeOH): 0.66

C. Synthesis of Carbamates

To a solution of 4,4'-thiodibenzene-1,3-diol (resorcinol sulphide, 5 g, 20 mmol, 4 eq.) in 40 ml of anhydrous THF and under nitrogen, are added drop by drop 0.88 ml of octyl isocyanate (5 mmol, 1 eq.) then the mixture is stirred for 9 hours under reflux. The reaction is followed by TLC.

After returning to room temperature, the solvent is evaporated then the residue extracted with an ethyl acetate/water mixture. The organic phase is washed twice with water then with a saturated NaCl solution. After drying over magnesium sulphate, a solid is obtained after evaporation of the solvent. The solid is washed with DCM then collected to provide starting resorcinol sulphide that has not reacted.

The filtrate (DCM) is then evaporated to lead to an oil purified on silica by a cyclohexane/ethyl acetate mixture or by preparative HPLC. The product obtained in the form of a colourless oil is dried under vacuum overnight. 540 mg are then obtained in the form of a colourless oil with a yield of 27%.

Example 24

2-(2,4-dihydroxyphenylthio)-5-hydroxyphenyl octylcarbamate

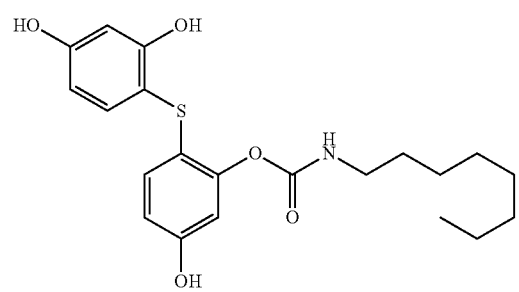 [SMILES: CCCCCCCCNC(=O)Oc1cc(O)ccc1Sc1ccc(O)cc1O]

$^1$H NMR (400 MHz, CDCl$_3$): δ: 0.86 (t, 3H); 1.26 (m, 8H); 1.35 (m, 2H); 1.59 (m, 2H); 3.32 (m, 2H); 5.30 (t, 1H); 5.93 (wide s, 1H); 6.23 (wide s, 1H); 6.35 (m, 2H); 6.41 (s, 1H); 6.52 (s, 1H); 6.63 (d, 1H); 7.32 (wide s, 1H); 7.35 (d, 1H).

MS (ESI+): 406.1 [M+H]$^+$

2) Synthesis of Analogues of Resorcinol Sulphoxide

Example 25(Resorcinol Sulphoxide)

4,4'sulphinyldibenzene-1,3-diol

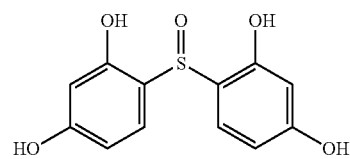 [SMILES: O=S(c1ccc(O)cc1O)c1ccc(O)cc1O]

$^1$H NMR (400 MHz, DMSO-d6): δ: 6.32 (m, 4H); 7.10 (d, 2H); 9.82 (wide s, 2H); 10.13 (wide s, 2H).

MS (APCI): 267.0 [M+H]$^+$

A) Synthesis of Esters

A suspension of 4,4'-sulphinylbis-1,3-benzenediol (resorcinol sulphoxide, 2.66 g, 10 mmol, 4 eq.) in 100 ml of anhydrous THF is solubilised hot and under nitrogen then are added after 5 minutes at room temperature, 420 µL of triethylamine (12 mmol, 1.2 eq.). A rapid precipitation is observed then 547 mg of lauroyl chloride (2.5 mmol, 1 eq.) are added drop by drop. The mixture is stirred for 2 hours at room temperature. The reaction is followed by TLC.

After returning to room temperature, the solid is filtered then the filtrate is evaporated to lead to an oil purified on silica by a heptane/ethyl acetate mixture (80/20 to 50/50) or by preparative HPLC. The product obtained in the form of a white solid is dried under vacuum overnight. 511 mg are then obtained with a yield of 46%.

Example 26

2-(2,4-dihydroxyphenylsulphinyl)-5-hydroxyphenyl dodecanoate

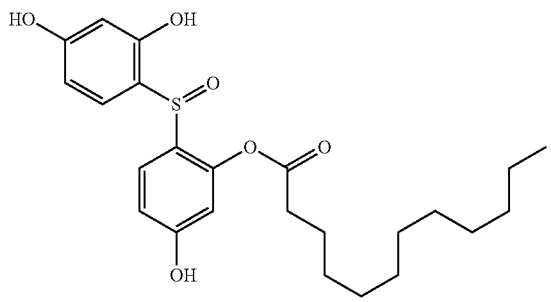 [SMILES: CCCCCCCCCCCC(=O)Oc1cc(O)ccc1S(=O)c1ccc(O)cc1O]

$^1$H NMR (400 MHz, DMSO-d6): δ: 0.86 (t, 3H); 1.24 (m, 16H); 1.53 (m, 2H); 2.45 (m, 2H); 6.28 (d, 1H); 6.33 (dd, 1H); 6.53 (s, 1H); 6.83 (dd, 1H); 7.12 (d, 1H); 7.43 (d, 1H); 9.88 (sl, 1H); 10.19 (sl, 1H); 10.27 (sl, 1H).

MS (APCI+): 449.2 [M+H]$^+$

Rf (1/1; Heptane/EtOAc): 0.42

Example 27

(9Z,12Z)-2-(2,4-dihydroxyphenylsulphinyl)-5-hydroxyphenyl octadeca-9,12-dienoate From linoleoyl chloride

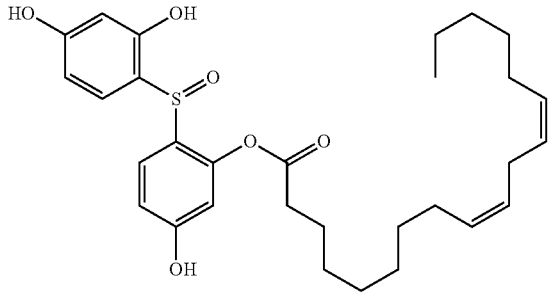 [SMILES: CCCCC/C=C\C/C=C\CCCCCCCC(=O)Oc1cc(O)ccc1S(=O)c1ccc(O)cc1O]

$^1$H NMR (400 MHz, DMSO-d6): δ: 0.84 (t, 3H); 1.29 (m, 14H); 1.55 (m, 2H); 2.00 (m, 4H); 2.42 (t, 2H); 2.76 (t, 2H); 5.33 (m, 4H); 6.28 (s, 1H); 6.35 (ds, 1H); 6.53 (s, 15 1H); 6.82 (d, 1H); 7.12 (d, 1H); 7.43 (d, 1H); 9.88 (s, 1H); 10.19 (s, 1H); 10.27 (s, 1H).

MS (ESI): 529.2 [M+H]$^+$

Rf (7/3; Heptane/EtOAc): 0.45

B) Synthesis of Ethers by Oxidation of Analogues of Resorcinol Sulphide

To a solution of example 12 (=4-(2-(decyloxy)-4-hydroxyphenylthio)benzene-1,3-diol) (320 mg) in 10 ml of acetic acid are added 260 µL of a solution of 30% hydrogen peroxide in H$_2$O (2.5 mmol, 3 eq.) then the mixture is stirred for 3 hours at room temperature.

50 mL of water are added to precipitate the product. The solid obtained is collected, then taken up in ethyl acetate then this organic phase is washed with water then with a saturated sodium chloride solution. After drying over MgSO$_4$, the solvent is evaporated to lead to a beige solid dried overnight in the vacuum oven (50 mbar, 50° C.). 310 mg of product are obtained with a yield of 90%.

Example 28

4-(2-(decyloxy)-4-hydroxyphenylsulphinyl)benzene-1,3-diol

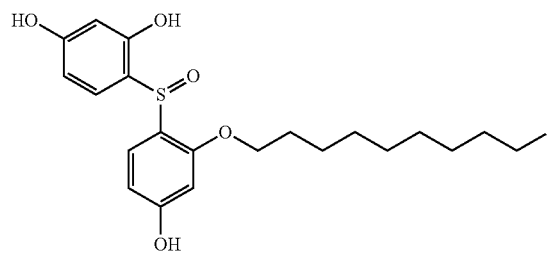 [SMILES: CCCCCCCCCCOc1cc(O)ccc1S(=O)c1ccc(O)cc1O]

$^1$H NMR (400 MHz, DMSO d6): δ: 0.86 (t, 3H); 1.23 (m, 14H); 1.54 (m, 2H); 3.77-3.92 (m, 2H); 6.26 (d, 1H); 6.29 (s, 1H); 6.40 (d, 1H); 6.49 (dd, 1H); 6.98 (d, 1H); 6.76 (s, 1H); 7.28 (d, 1H); 9.80 (s, 1H); 9.98 (s, 1H); 10.06 (s, 1H).

$^{13}$C NMR (100 MHz, DMSO d6): δ: 13.89; 22.03; 25.14; 25.38; 28.29; 28.64; 28.66; 28.90; 28.93; 31.25; 67.86; 99.86; 102,38; 107.12; 107.49; 120.17; 121.72; 127.19; 127.68; 156.82; 157.07; 160.95; 161.18.

MS (ESI+): 407.2 [M+H]$^+$

Rf (1/1; Heptane/EtOAc): 0.12

3) Synthesis of Analogues of Resorcinol Sulphone

A) Synthesis of Resorcinol Sulphone

To a solution of 4,4'-thiodibenzene-1,3-diol (resorcinol sulphide, 10 mmol, 2.5g) in an acetone/acetic acid mixture (1/1, 60 mL) are added 5.12 mL of a 30% solution of hydrogen peroxide in H$_2$0 (30 mmol) then the mixture is stirred for 72 hours at room temperature.

The solvent is evaporated then the solid obtained is taken up in ethyl acetate to obtain a white solid. Filtration of the solid then the filtrate is evaporated then the residue thereby obtained is purified on silica to lead to 320 mg of a white solid.

Example 29

4,4'-sulphonyldibenzene-1,3-diol (Resorcinol Sulphone)

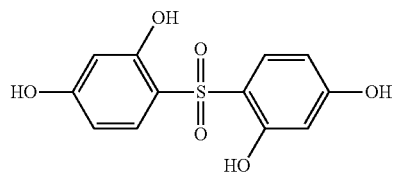 [SMILES: O=S(=O)(c1ccc(O)cc1O)c1ccc(O)cc1O]

$^1$H NMR (400 MHz, DMSO-d6): 6: 6.24 (d, 2H); 6.33 (dd, 2H); 7.61 (d, 2H); 10.06 5 (s, 1H); 10.16 (s, 1H).

$^{13}$C NMR (100 MHz, DMSO d6): 5:102.73; 106.41; 117.98; 131.54; 157.14; 162.86.

Rf (9/1; DCM/MeOH): 0.6

B) Synthesis of Analogues of Resorcinol Sulphone by Oxidation of Analogues of Resorcinol Sulphide into Resorcinol Sulphone To a solution of example 12 (=4-(2-(decyloxy)-4-hydroxyphenylthio)benzene-1,3-diol) (195 mg, 0.5 mmol) in 10 ml of acetic acid are added 2.8 mL of a 30% solution of hydrogen peroxide in $H_2O$ (25 mmol, 50 eq.) then the mixture is stirred for 48 hours at room temperature.

50 mL of water are added to precipitate the product. The solid obtained is collected on sinter, then washed twice with water then twice with n-pentane. The solid is then dried overnight in the vacuum oven (50 mbar, 50° C.) to lead to a white solid. 135 mg of product are obtained with a yield of 64%.

Example 30

4-(2-(decyloxy)-4-hydroxyphenylsulphonyl)benzene-1,3-diol

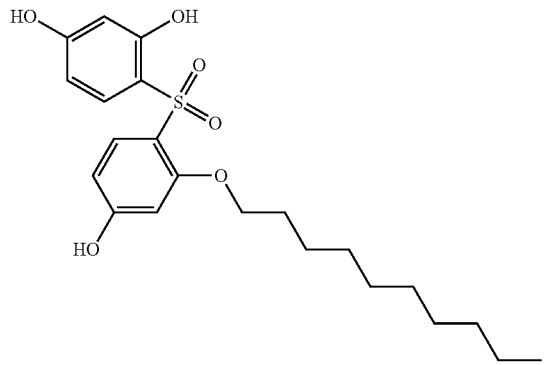 [SMILES: CCCCCCCCCCOc1cc(O)ccc1S(=O)(=O)c1ccc(O)cc1O]

$^1$H NMR (400 MHz, DMSO d6): 5: 0.87 (tl, 3H); 1.26 (m, 14H); 1.44 (ml, 2H); 3.77 (ml, 2H); 6.22 (s, 1H); 6.30 (d, 1H); 6.35 (s, 1H); 6.44 (d, 1H); 7.59 (d, 1H); 7.74 (d, 1H); 9.97 (s, 1H); 10.10 (s, 1H); 10.30 (s, 1H).

$^{13}$C NMR (100 MHz, DMSO d6): 6:13.89; 22.02; 25.29; 28.25; 28.64; 28.75; 28.88; 28.92; 31.24; 67.96; 99.78; 102.66; 106.04; 106.28; 117.91; 119.88; 131.65; 131.82; 156.97; 157.69; 162.77; 163.15.

II Results of Biological Tests

1) Protocols

A) Determination of the Depigmenting Activity in an in vitro Acellular Test: Tyrosinase Inhibition Test)
Principle:

This test is used to evaluate the depigmenting activity of the molecules tested. Tyrosinase is a limiting enzyme in melanogenesis.

It belongs to the family of oxydoreductases. It has in particular the function: monophenol monooxygenase (MPMO) and polyphenol oxidase (PPO).

It is synthesised at the level of the melanocytes. It is activated during its migration towards melanosome keratinocytes. It transforms tyrosine into DOPA then dopaquinone, which leads in fine to a polymerisation, i.e. a production of pigments (see diagram below).

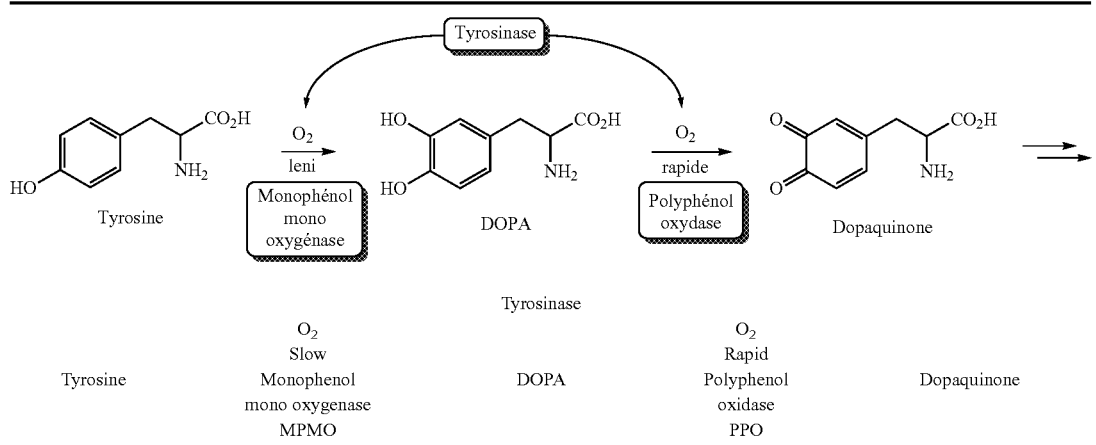

The substrate: L-tyrosine, is transformed into L-DOPA by the monophenol mono oxygenase function which is transformed by the polyphenol oxidase function from tyrosinase into dopaquinone. The latter is going to self-oxidise into dopachrome which is measured by spectrophotometry at 490 nm.

More precisely, it is the overall tyrosinase activity (MP-MOg) which is measured since it is the dopachrome in fine that is assayed. Thus the products tested on MPMOg (=measurement of the activity on PPO and MPMO) can cumulate the inhibition of the 2 functions, inhibiting uniquely the MPMO function stricto sensus (transformation of tyrosine into DOPA) as a complement to the PPO test, could inhibit PPO uniquely.

General Experimental Conditions:

Reader: Synergy HT programme: tyrosinase 280-490 kinetic: kinetic over 45 min, reading at t=10 minutes, Tests in 96 transparent wells, Phosphate buffer—pH 6.8, Enzyme: mushroom tyrosinase—Sigma=T-3824 Substrate: L-Tyrosine—Sigma=T-3754, Positive control: Kojic acid (KA)—Fluka=60890 (reference inhibitor)

Reference Molecules for the Test:

Kojic acid: 9 µM<IC 50<20 µM (PPO), 3 µM<IC 50<7 µM (MPMO)

Vitamin C: 20 µM<IC 50<40 µM (PPO)

Reduced glutathion: 55% inhibition at 25 µM (PPO), IC 50=1-2 µM (MPMO)

Hydroquinone: IC 50=3-4 µM (MPMO)

Arbutin: 57% inhibition at 88 µM (MPMO)

These exogenous molecules are known to regulate negatively melanogenesis. Hydroquinone inhibits the synthesis of melanin by presenting itself as tyrosinase substrate in order to divert its activity. Arbutin containing hydroquinone acts in the same way. Kojic acid reduces the activity of tyrosinase by inhibiting the hyperpigmentation induced by the UV. Vitamin C would inhibit tyrosinase but would also behave as a powerful reducer by preventing the coloration of the melanin through oxidation. Vitamin A decreases the expression of tyrosinase.

B) Melanin Assay Test in B16-F10 Cells:

Principle:

This involves a test of measuring the synthesis of melanin by colorimetric assay on a murine melanoma cell line: the B16-F10 line. This test makes it possible to evaluate the depigmenting power of active ingredients.

The B16-F10 cells are cultured in 96-well plates in DMEM medium supplemented with FCS (foetal calf serum), and incubated for 24 hours at 37° C., 5% $CO_2$. The cells are then stimulated with 0.1 µM α-MSH (to stimulate the synthesis of melanin, the stimulation observed is around 150%) and treated for 72 hours with the active ingredients to be tested. Each concentration of active ingredient is tested at least in triplicate. The total melanin followed by the intracellular melanin dissolved in the lysis buffer are then assayed by absorbance reading at 405 nm. The total proteins are assayed in the lysate and the results are expressed in mg melanin/mg proteins. The percentage of activity is calculated as follows:

A negative value indicates an inhibition, whereas a positive value indicates an induction of the synthesis of melanin.

General Experimental Conditions:

Equipment:

CO2 cell incubator (Heraeus), Oven, Centrifuge (Heraeus), Laminar air flow fume hood, 96-well clear bottomed plates—Falcon, sterile cones—Treff Lab, Polylabo, Mithras LB940 (Berthold Technologies)—154/MIPA/003

Biological Equipment:

B16-F10 cell line between P10 and P20 (murine melanocytes) (ATCC, CRL-6475)

Reagents:

DMEM without phenol red (GibcoBRL, 31053-028), 200 mM Glutamax-I Supplement (GibcoBRL, 35050-038), D-PBS (GibcoBRL, 14190-094), Foetal calf serum (Invitrogen, 10270-098), Trypsine-EDTA (GibcoBRL, 25300-054), NaOH (Sigma, S8045-500G), DMSO (Sigma, 471267-1L), Nle, Phe—Melanocyte Stimulating Hormone (Sigma, M-8764), Melanin (Sigma, M-0418), BCA-Copper (Sigma, B9643 and C2284), BSA (Sigma, P0914)

C) Test for the Study of the Antioxidant Capacity by Chemiluminescence (Photochem Analytik Jena)

Principle:

This test is used to determine the antioxidant capacity of the molecules. It is a method that generates free radicals by a photochemical signal. The intensity of the oxidation is 1000 times greater than that obtained under normal conditions.

The detection is carried out by chemiluminescence. It enables the evaluation of hydrosoluble and liposoluble antioxidant molecules or extracts.

The results are expressed respectively in equivalent quantity of vitamin C or Trolox (6-hydroxy-2,5,7,8-tetramethylchroman-2-carboxylic acid). The sensitivity is of the order of a nanomole.

The antioxidant activity studied in this test represents the capacity to trap specifically superoxide anions by chemiluminescence.

The quantified results are expressed in Trolox equivalent (standard), i.e. in "µg of product for 1 µg of Trolox". This signifies that a quantity×of sample is needed to obtain an activity equivalent to the activity detected for 1 µg of standard. It is an anti-oxidant power relative to a reference, which makes it possible to disregard the concentration tested.

Generation of Oxygenated Free Radicals:

The superoxide radical: $O_2^{0-}$ is generated by a photochemical reaction:

$$L + h\nu \text{ (UV)} + O_2 \rightarrow L^*O_2 \rightarrow L^{0+} + O_2^{0-}$$

L*: luminol in the excited state $L^0+$: luminol radical

Detection of the Signal:

A part of the superoxide anions is quenched by the antioxidants. The remaining free radicals are quantified by chemiluminescence.

$$L^{0+} + O_2^{0-} \rightarrow N_2 + AP^{*2-} \rightarrow AP^{2-} + h\nu \text{ (luminescence)}$$

$AP^{*2-}$: aminophthalate in the excited state $$\% \text{ activity} = \frac{\text{Normalised average of control} - \text{Normalised average of treated}}{\text{Normalised average of control}} \times 100$$

| Name | Conditions | Photo-sensitising | Antioxidant |
|---|---|---|---|
| Blank | 100% $O_2$ generated | + | — |
| Standards | Standard range: from 1 to 3 nmol | + | Vitamin C or Trolox |
| Test | +/−$O_2^{0-}$ generated | + | Molecule x to be tested |

D) Test of Protection of Linoleic Acid Following a UV Stress. Target: Protection of Linoleic Acid Under Fenton Conditions, UV Irradiation Linoleic acid belongs to the family of polyunsaturated fatty acids (PUFA) (AGPI). Sensitive to oxidation, linoleic acid is a favoured target for oxygenated free radicals (OFR) in biological media. When biological membranes are exposed to an oxidative stress, the components the most affected are the phospholipids constituted of PUFA and cholesterol. Their degradation leads to lipidic peroxidation and generally to destructuring. Lipidic peroxidation is a self-catalysing process which generally involves OFR. Lipidic peroxidation is in part responsible for skin ageing.

The method employed to evaluate lipid peroxidation is based on the coupling of thiobarbituric acid (TBA) and secondary degradation products leading to coloured compounds detectable by spectrofluorometry. The essential secondary compound of final degradation is malondialdehyde, MDA. MDA is a carcinogenic and mutagenic aldehyde, it acts on proteins and DNA.

Principle of the Test:

The sample to be tested is placed in contact with linoleic acid in a weight/weight ratio. The sample undergoes an MED (Minimal Erythemal Dose) irradiation under Fenton conditions, namely in the presence of $H_2O_2$ and iron II in a solar simulator.

Following irradiation, the reaction mixture is taken up in methanol and derivatised at 90° C. with TBA. Chromogene, the MDA-TBA complex, representative of the equimolar production of MDA is assayed by fluorimetry (excitation at 525 nm, emission at 549 nm).

The results are expressed in fluorescence units, as a function of a MDA-TBA control range then expressed as concentration of the MDA-TBA complex. Then, the percentage of the starting MDA/linoleic acid (LA) ratio is determined. Then the percentage of protection of linoleic acid is determined.

E) Determination of the Minimal Inhibitory Concentration (MIC):

This test is used to determine the antibacterial activity of a compound. Tests are carried out with 4 bacterial strains using the principle of microdilution. The MIC are determined by micromethod in liquid medium. The successive dilutions according to the products tested in the culture broth (Trypcase soy) are carried out on 96 well microplates in a final volume of 0.1 ml. The wells are seeded with 0.01 ml of bacterial suspensions titrated at around $10^7$ UFC/ml. The microplates are incubated under optimal growth conditions and the MIC is read visually.

2) Results

A) Determination of the Depigmenting Activity in an in vitro Acellular Test: Tyrosinase Inhibition Test.

All of the results have been grouped together in summary Table 1 inserted hereafter.

Caption of results for tyrosinase test:

| Interesting activity+++ | Very good activity | >80% assay from 250 to 150 µM |
| Interesting activity++ | Good activity | >30% assay from 250 to 150 µM |

B) Melanin Assay Test in B16-F10 Cells:

The results have also been grouped together in summary Table 1 below.

Interpretation of results:

A negative value indicates an inhibition, whereas a positive value indicates an induction of the synthesis of melanin.

It may be noted that the majority of the compounds tested exhibit good inhibition capacity of the synthesis of melanin. The invention thus relates to the cosmetic use for the depigmentation of the skin of compounds of generic formula (I) or (I').

C) Test for the Study of the Antioxidant Capacity by Chemiluminiscence (Photochem Analytic Jena)

The results have also been grouped together in summary Table 1 below.

The majority of the compounds have good antioxidant activity. The scale for interpreting the results is the following:

| Products | µg of sample for 1 µg of Trolox | Activity |
|---|---|---|
| Vitamin C | 0.1 to 3.0 | Very good |
| BHT | 3.01 to 50 | Good |
| Cysteine | 50.1 to 1000 | Medium |
| Albumin | >1000 | Low |
| Lipoic acid | NEGATIVE | None |

Most of the compounds exhibit results comparable to vitamin C. All of the compounds show results less than 1000 µg of Trolox (301 µg being the lowest result obtained with resorcinol sulphone); they thus all have interesting anti-oxidant activity. The invention also relates to the cosmetic use for the prevention and/or treatment of the ageing of the skin of compounds of generic formula (I) or (I').

D) Test of Protection of Linoleic Acid Following a UV Stress

The results have also been grouped together in summary Table 1 below. The negative control is linoleic acid non stressed by UV radiation and chemically: thus not irradiated (NI). It is representative of the basal oxidation linked to the environment. It corresponds to the basal non specific production of MDA, and is very low (of the order of 7 10E-7 M).

The positive control is quercetin which has an almost total protection at 1% and which protects partially (around 50%) at 0.1%.

The product assay is expressed as weight/weight ratio, in other words in weight percentage with respect to the total quantity of linoleic acid. The maximal MDA level is determined by the condition UV+$H_2O_2$+iron II (F).

The percentage of protection of linoleic acid represents: the % ratio of MDA under maximal stress conditions untreated over the % of MDA under stress conditions treated by the product.

A molecule is considered as significantly active if its percentage of protection of linoleic acid is greater than 20%. All of the molecules tested are thus significantly active.

TABLE 1

| Example | Tyrosinase depigmenting activity result | B16 activity results -% at X µM | µg of sample for 1 µg of Trolox | % Protection Linoleic acid under UV/Fenton |
|---|---|---|---|---|
| Example 1 | +++ | -50% (61 µM) 1 µM | 23 | 90% |
| Example 2 | ++ | -50% (14 µM) | 9.7 | 92% |
| Example 3 | +++ | -41% (20 µM) | 4.7 | 87% |
| Example 4 | +++ | -35% (10 µM) | 5.2 | 89% |
| Example 5 | +++ | -27% (20 µM) | 2.8 | 89% |
| Example 6 | +++ | -30% (20 µM) | 14.9 | — |
| Example 7 | +++ | -50% (10 µM) | 3.4 | 92% |
| Example 8 | +++ | -40% (10 µM) | 18.8 | 97% |
| Example 9 | +++ | -31% (20 µM) | 3.2 | 85% |
| Example 10 | +++ | -20% (20 µM) | 22 | 94% |
| Example 11 | +++ | -34% (20 µM) | 3.5 | 91% |
| Example 12 | +++ | — | 3.4 | 96% |
| Example 13 | - | — | 5.7 | 95% |
| Example 14 | +++ | -50% (48 µM) 7 µM | 4.8 | — |
| Example 15 | ++ | -20% (10 µM) | 30 | 75% |
| Example 16 | +++ | — | 33.2 | 91% |
| Example 17 | +++ | -50% (92 µM) | 3.9 | 87% |
| Example 18 | +++ | -20% (50 µM) | 24.1 | 90% |
| Example 19 | +++ | -20% (50 µM) | 2.8 | 88% |
| Example 20 | +++ | -24% (50 µM) | 25.6 | 91% |
| Example 21 | +++ | -50% (32 µM) 11 µM | 5.9 | — |
| Example 22 | +++ | — | 2.5 | 97% |
| Example 23 | +++ | — | 2.8 | 96% |
| Example 24 | +++ | -26% (50 µM) | 3.8 | 97% |
| Example 25 | +++ | -50% (73 µM) 12 µM | 73 | 79% |
| Example 26 | +++ | — | 69 | 80% |
| Example 27 | +++ | — | 40 | 78% |
| Example 28 | ++ | — | 28 | 94% |
| Example 29 | - | — | 301 | 25% |
| Example 30 | - | — | 147 | 34% |

E) Determination of the Minimum Inhibitory Concentration (MIC):

The results have been grouped together in Table 2. A compound is considered to have very good antibacterial activity when it has an MIC below 1 ppm. The antibacterial activity is considered as good when the MIC is between 1 ppm and 100 ppm. The antibacterial activity of a compound is considered as average when it is between 100 ppm and 1000 ppm.

TABLE 2

| Bacterial strains | Example 5 | Example 7 | Example 12 | Example 13 |
|---|---|---|---|---|
| Staphylococcus aureus IP4.83 ATCC6538 | 6 ppm | 0.78 ppm | 0.78 ppm | 190 ppm |
| Staphylococcus epidermidis IP6821 | 3 ppm | 0.39 ppm | 0.39 ppm | 156 ppm |
| P. acnes IP53.117 ATCC6919 | 3 ppm | 0.09 ppm | 0.09 ppm | 90 ppm |
| Escherichia coli IP53126 ATCC8739 | — | 390 ppm | 780 ppm | — |

The compounds tested exhibit significant antibacterial activity. In particular, examples 7 and 12 exhibit strong antibacterial activity against the strain *Propionibacterium acnes*.

III. Composition According to the Invention

| Ingredients (trade name) | INCI designation | Percentage by weight | Function |
|---|---|---|---|
| I. Purified water | Water | SQF 100% | |
| Hydrolite 5 | Pentylene Glycol | 3 | Humectant, Preservative |
| EDTA, 2Na | Disodium EDTA | 0.1 | Complexing agent |
| Microcare PM4 | Phenoxyethanol - Parabene | 0.8 | Preservatives |
| Water soluble PCL | Trideceth-9 & PEG-5 Ethylhexanoate | 1.5 | Aqueous emollient |
| II. Pemulen TR-1 | Acrylates/C 10-30 Alkyl Crosspolymer | 0.5 | Gelifier, stabilising agent |
| III. Stearine TP | Stearic acid | 2 | Emulsifier, consistency factor |
| Liquid PCL | Cetearylethyl-hexanoate & Isopropyl-myristate | 3 | Emollient |
| DC200 | Dimethicone | 0.3 | Emollient |
| Myritol 318 | Capric or caprylic triglycerides | 3 | Emollient |
| Primol 352 | Liquid paraffin | 2 | Emollient |
| IV. Depigmenting active ingredient | | | Active ingredient |
| V. Sodium hydroxide | NaOH | 0.08 | pH adjuster |

In such a composition, the percentage of active ingredient can vary between 0.01% and 10% by weight and preferably from 0.1% to 5% by weight with respect to the total weight of the composition.

The invention also relates to pharmaceutical or cosmetic compositions comprising at least one of the compounds of formula (I) or formula (I') in association with at least one pharmaceutically or cosmetically acceptable excipient.

According to a specific embodiment of the invention, the pharmaceutical or cosmetic compositions comprise at least one of the compounds of formula (I) or formula (I') in association with at least one pharmaceutically or cosmetically acceptable excipient and a fatty phase.

According to a specific embodiment of the invention, the pharmaceutical or cosmetic compositions comprise at least one of the compounds of formula (I) or formula (I') in association with at least one pharmaceutically or cosmetically acceptable excipient and an emollient.

The present invention relates to a cosmetic composition for depigmenting the skin and/or head hair and/or body hair characterised in that it comprises at least one compound of formula (I) or formula (I').

The invention also relates to a cosmetic composition for anti-ageing of the skin, characterised in that it comprises at least one compound of formula (I) or formula (I').

The invention also extends to a pharmaceutical composition for disinfecting the skin characterised in that it comprises at least one compound of formula (I).

The composition according to the invention may moreover comprise conventional cosmetic adjuvants especially chosen from fatty phases, organic solvents, thickeners, softeners, opacifiers, stabilisers, emollients, anti-foaming agents, hydrating agents, fragrances, preservatives such as parabenes, polymers, fillers, sequestering agents, bactericides, odour absorbers, alkalising or acidifying agents, surfactants, anti-free radicals, antioxidants, vitamins E and C, a-hydroxyacids, or thermal water such as Avène thermal water or any other ingredient normally used in cosmetics, in particular for the production of compositions of this type. The composition according to the invention may moreover comprise a fatty phase. The fatty phase may be constituted of an oil or a wax or mixtures thereof, and also comprise fatty acids, fatty alcohols, and fatty acid esters. The oils may be chosen from animal, plant, mineral or synthetic oils and especially from vaseline oil, paraffin oil, silicone oils, volatile or not, such as dimethicone; isoparaffins, polyolefins, fluorinated and perfluorinated oils. Similarly, the waxes may be chosen from animal, fossil, plant or synthetic waxes such as bee waxes, candelilla waxes, canuba waxes, karate butter, petroleum wax (or microcrystalline wax), paraffin, and mixtures thereof. The composition according to the invention may moreover comprise a polyol miscible in water at room temperature (around 25° C.), especially chosen from polyols having particularly from 2 to 20 carbon atoms, preferably having from 2 to 10 carbon atoms, and preferentially having 2 to 6 carbon atoms, such as glycerine; glycol derivatives such as propylene glycol, butylene glycol, pentylene glycol, hexylene glycol, dipropylene glycol, diethylene glycol; glycol ethers such as $C_1$-$C_4$ mono-, di- or tri-propylene glycol alkyl ethers, $C_1$-$C_4$ mono-, di- or tri-ethylene glycol alkyl ethers; and mixtures thereof.

The composition according to the invention may also comprise thickening agents or rheology modification agents, such as for example non ionic ethoxylated hydrophobically modified urethanes, polycarboxylic acid thickeners such as copolymers of acrylates/steareth-20 methacrylate, carbomers, cured acrylate copolymers and mixtures thereof.

The composition according to the invention may also comprise acids and bases making it possible to adjust the pH range of said composition. The bases may be inorganic (sodium hydroxide, potassium hydroxide, aqueous ammonia, etc.) or organic such as mono-, di- or tri-ethanolamine, aminomethylpropanediol, N-methyl-glucamine, basic amino acids such as arginine and lysine, and mixtures thereof.

The composition according to the invention may also comprise skin conditioning agents. Examples of skin conditioning agents include, but are not limited to, anionic, cationic and non ionic emulsifiers such as sodium lauryl sulphate, sodium dioctyl sulphosuccinate, sodium stearate, sorbitan ester; ethoxylated fatty acids; ethoxylated fatty alcohols such as tridecet-9 and PEG-5 ethylhexanoate; stearic acid; any other emulsifier and conditioning agent known to those skilled in the art; and mixtures thereof.

The composition according to the invention may moreover contain other active ingredients leading to a complementary effect.

The composition according to the invention may be presented in any form appropriate for topical application, particularly on the skin and/or the hair. In particular, they can come in the form of emulsions obtained by the dispersion of an oil phase in an aqueous phase, for example an oil-in-water or water-in-oil or multiple emulsion, or in the form of a gel or a liquid, paste or solid anhydrous product, or in the form of a dispersion in the presence of spherules. The composition according to the invention may also be less fluid and come in the form of a white or coloured cream, an ointment, a milk, a lotion, a serum, a paste, a mask, a powder, a solid stick, or, optionally, an aerosol, a foam or a spray.

The invention claimed is:
1. Compound of generic formula (I)

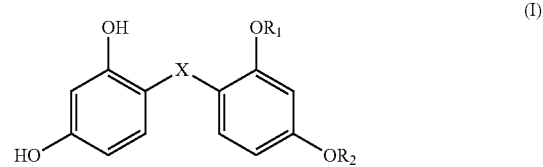

in which:
X=S, SO or $SO_2$ and;
one of the radicals $R_1$ and $R_2$ represents a hydrogen atom and the other a radical selected from:
  a $C_1$ to $C_{18}$ linear or branched alkyl, optionally substituted by one or more halogen atoms,
  a $C_2$ to $C_{18}$ linear or branched alkenyl, optionally substituted by one or more halogen atoms, or
  an aralkyl, optionally substituted by one or more $C_1$ to $C_6$ alkoxy groups, or
  $COR_3$ or $CONHR_3$, but not simultaneously,
    wherein $R_3$ represents a radical selected from:
    a $C_1$ to $C_{18}$ linear or branched alkyl, optionally substituted by one or more halogen atoms,
    a $C_2$ to $C_{18}$ linear or branched alkenyl, optionally substituted by one or more halogen atoms,
    an aralkyl, optionally substituted by one or more $C_1$ to $C_6$ alkoxy groups,
    an aralkenyl, optionally substituted by one or more $C_1$ to $C_6$ alkoxy groups and/or one or more OH groups,
  or
    an aryl radical, optionally substituted by one or more $C_1$ to $C_6$ alkoxy groups.

2. Compound according to claim 1, wherein X=S.
3. Compound according to claim 1, wherein X=S and $R_2$=H.
4. Compound according to claim 3, wherein X=S, $R_2$=H and $R_1$ is selected from the group consisting of: $C_1$ to $C_{18}$ linear or branched alkyl, $C_2$ to $C_{18}$ linear or branched alkenyl, $COR_3$ and $CONHR_3$ as defined in claim 1.
5. Compound according to claim 1, wherein $R_1$ represents:
  a $C_1$ to $C_8$ linear or branched alkyl; or
  a $C_2$ to $C_{18}$ linear or branched alkenyl selected from an allyl group or a 3,3 dimethylallyl group or a geranyl group or a farnesyl group; or
  a benzyl.

6. Compound according to claim 1, wherein $R_3$ represents:
a $C_7$ to $C_{15}$ linear or branched alkyl; or
a $C_{10}$ to $C_{18}$ linear or branched alkenyl; or
a benzyl; or
an aralkenyl selected from phenyl acrylate or (4-methoxyphenyl)acrylate or (3,4-dimethoxyphenyl)acrylate; or
a phenyl.

7. Compound according to claim 1, selected from one of the following compounds:
- 4-(4-hydroxy-2-((2E,6E)-3,6,11-trimethyldodeca-2,6,10-trienyloxy)phenylthio)benzene-1,3-diol,
- 4-(4-hydroxy-2-(3-methylbut-2-enyloxy) phenylthio) benzene-1,3-diol,
- (E)-4-(2-(3,7-dimethylocta-2,6-dienyloxy)-4-hydroxyphenylthio)benzene- 1,3-diol,
- 4-(2-butoxy-4-hydroxyphenylthio)benzene-1,3-diol,
- 4-(4-butoxy-2-hydroxyphenylthio)benzene-1,3-diol,
- 4-(4-hydroxy-2-(octyloxy)phenylthio)benzene-1,3-diol,
- 4-(2-hydroxy-4-(octyloxy)phenylthio)benzene-1,3-diol,
- 4-(2-(benzyloxy)-4-hydroxyphenylthio)benzene-1,3-diol,
- 4-(4-(benzyloxy)-2-hydroxyphenylthio)benzene-1,3-diol,
- 4-(4-hydroxy-2-(4methoxybenzyloxy) phenylthio) benzene-1,3-diol,
- 4-(2-(decyloxy)-4-hydroxyphenylthio)benzene-1,3-diol,
- 4-(2-(hexadecyloxy)-4-hydroxyphenylthio)benzene-1,3-diol,
- 2-(2,4-dihydroxyphenylthio)-5-hydroxyphenyl dodecanoate,
- 2-(2,4-dihydroxyphenylthio)-5-hydroxyphenyl octanoate,
- 4-(2,4-dihydroxyphenylthio)-3-hydroxyphenyloctanoate,
- 2-(2,4-dihydroxyphenylthio)-5-hydroxyphenyl 3-phenylpropanoate,
- 4-(2,4-dihydroxyphenylthio)-3-hydroxyphenyl 3-phenylpropanoate,
- 2-(2,4-dihydroxyphenylthio)-5-hydroxyphenyl 3-methylbutanoate,
- 4-(2,4-dihydroxyphenylthio)-3-hydroxyphenyl 3-methylbutanoate,
- (9Z,12Z)-2-(2,4-dihydroxyphenylthio)-5-hydroxyphenyl octadeca-9,12-dienoate
- (E)-2-(2,4-dihydroxyphenylthio)-5-hydroxyphenyl 3-(4-methoxyphenyl)acrylate,
- (E)-2-(2,4-dihydroxyphenylthio)-5-hydroxyphenyl 3-(3,4-dimethoxyphenyl)acrylate,
- 2-(2,4-dihydroxyphenylthio)-5-hydroxyphenyl octylcarbamate,
- 2-(2,4-dihydroxyphenylsulphinyl)-5-hydroxyphenyl dodecanoate,
- (9Z, 12Z)-2-(2,4-dihydroxyphenylsulphinyl)-5-hydroxyphenyl octadeca-9,12- dienoate
- 4-(2-(decyloxy)-4-hydroxyphenylsulfinyl)benzene-1,3-diol,
- 4-(2-(decyloxy)-4-hydroxyphenylsulphonyl)benzene-1,3-diol, or
- 2-(2,4-dihydroxyphenylthio)-5-hydroxyphenyl palmitate.

8. A method of bleaching and/or lightening of the human skin and/or body hair and/or head hair comprising the application on the skin and/or body hair and/or head hair of a compound of formula (I')

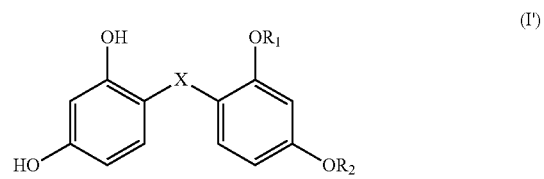

in which X=S or SO and the radicals $R_1$ and $R_2$ simultaneously represent hydrogen or one of the radicals $R_1$ and $R_2$ represents a hydrogen atom and the other a radical selected from:
- a $C_1$ to $C_{18}$ linear or branched alkyl, optionally substituted by one or more halogen atoms
- a $C_2$ to $C_{18}$ linear or branched alkenyl, optionally substituted by one or more halogen atoms, or
- an aralkyl, optionally substituted by one or more $C_1$ to $C_6$ alkoxy groups, or
- $COR_3$, or
- $CONHR_3$,
  wherein $R_3$ represents a radical selected from:
  - a $C_1$ to $C_{18}$ linear or branched alkyl, optionally substituted by one or more halogen atoms,
  - a $C_2$ to $C_{18}$ linear or branched alkenyl, optionally substituted by one or more halogen atoms,
  - an aralkyl, optionally substituted by one or more $C_1$ to $C_6$ alkoxy groups,
  - an aralkenyl, optionally substituted by one or more $C_1$ to $C_6$ alkoxy groups and/or one or more OH groups, or
- an aryl radical, optionally substituted by one or more $C_1$ to $C_6$ alkoxy groups.

9. A method of cosmetic treatment of the ageing of the skin comprising the application on the skin of a compound of formula (I')
(I')
in which X=S, SO or $SO_2$ and;
$R_1$ and $R_2$ are simultaneously hydrogen or one of the radicals $R_1$ and $R_2$ represents a hydrogen atom and the other a radical selected from:
- a $C_1$ to $C_{18}$ linear or branched alkyl, optionally substituted by one or more halogen atoms,
- a $C_2$ to $C_{18}$ linear or branched alkenyl, optionally substituted by one or more halogen atoms, or
- an aralkyl, optionally substituted by one or more $C_1$ to $C_6$ alkoxy groups, or
- $COR_3$, or
- $CONHR_3$,
  wherein $R_3$ represents a radical selected from:
  - a $C_1$ to $C_{18}$ linear or branched alkyl, optionally substituted by one or more halogen atoms,
  - a $C_1$ to $C_{18}$ linear or branched alkenyl, optionally substituted by one or more halogen atoms,
  - an aralkyl, optionally substituted by one or more $C_1$ to $C_6$ alkoxy groups,
  - an aralkenyl, optionally substituted by one or more $C_1$ to $C_6$ alkoxy groups and/or one or more OH groups, or
- an aryl radical, optionally substituted by one or more $C_1$ to $C_6$ alkoxy groups.

10. A method of disinfecting the skin comprising the application on the skin of a person in need thereof of a compound of formula (I) as an antibacterial active ingredient

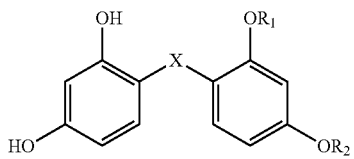

wherein X=S, one of the radicals $R_1$ and $R_2$ represents a hydrogen atom and the other a $C_1$ to $C_{18}$ linear alkyl.

11. Pharmaceutical or cosmetic composition comprising as active ingredient at least one compound of formula (I) as defined according to claim 1, in association with a pharmaceutically or cosmetically acceptable excipient.

12. Pharmaceutical or cosmetic composition according to claim 11, wherein the quantity of compound of formula (I) varies between 0.01% and 10% by weight with respect to the total weight of the composition.

13. A method of depigmenting the skin and/or head hair and/or body hair comprising the application on the skin of a cosmetic composition or a composition comprising at least one compound of formula (I')

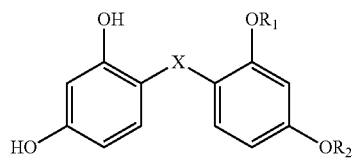

in which X=S or SO and;

$R_1$ and $R_2$ both represent a hydrogen atom or one of $R_1$ and $R_2$ represents a hydrogen atom and the other represents radical selected from:

a $C_1$ to $C_{18}$ linear or branched alkyl, optionally substituted by one or more halogen atom(s), a $C_2$ to $C_{18}$ linear or branched alkenyl, optionally substituted by one or more halogen atom(s), or an aralkyl, optionally substituted by one or more $C_1$ to $C_6$ alkoxy group(s), or $COR_3$ or $CONHR_3$, wherein $R_3$ represents a radical selected from:

a $C_1$ to $C_{18}$ linear or branched alkyl, optionally substituted by one or more halogen atoms, a $C_2$ to $C_{18}$ linear or branched alkenyl, optionally substituted by one or more halogen atoms, an aralkyl, optionally substituted by one or more $C_1$ to $C_6$ alkoxy groups, an aralkenyl, optionally substituted by one or more $C_1$ to $C_6$ alkoxy groups and/or one or more OH groups, or an aryl radical, optionally substituted by one or more $C_1$ to $C_6$ alkoxy groups.

14. A method of cosmetic treatment of the ageing of the skin comprising the application on the skin of a composition comprising at least one compound of formula (I')

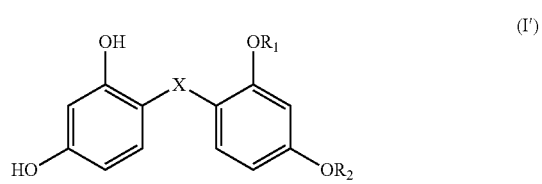

in which X=S, SO or $SO_2$ and;

$R_1$ and $R_2$ both represent a hydrogen atom or one of $R_1$ and $R_2$ represents a hydrogen atom and the other represents radical selected from:

a $C_1$ to $C_{18}$ linear or branched alkyl, optionally substituted by one or more halogen atoms, a $C_2$ to $C_{18}$ linear or branched alkenyl, optionally substituted by one or more halogen atoms, or an aralkyl, optionally substituted by one or more $C_1$ to $C_6$ alkoxy groups, or $COR_3$ or $CONHR_3$, wherein $R_3$ represents a radical selected from:

a $C_1$ to $C_{18}$ linear or branched alkyl, optionally substituted by one or more halogen atoms, a $C_2$ to $C_{18}$ linear or branched alkenyl, optionally substituted by one or more halogen atoms, an aralkyl, optionally substituted by one or more $C_1$ to $C_6$ alkoxy groups, an aralkenyl, optionally substituted by one or more $C_1$ to $C_6$ alkoxy groups and/or one or more OH groups, or an aryl radical, optionally substituted by one or more $C_1$ to $C_6$ alkoxy groups.

15. A method of disinfecting the skin comprising the application on the skin of a pharmaceutical composition comprising a compound of formula

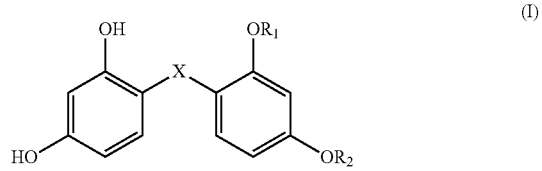

wherein X=S, one of the radicals $R_1$ and $R_2$ represents a hydrogen atom and the other a $C_1$ to $C_{18}$ linear alkyl to a person in need thereof.

16. Method of preparing a compound of generic formula (I) according to claim 1, wherein 4,4'-thiodibenzene-1,3-diol or 4,4'-sulphinylbis-1,3-benzenediol is reacted with a halide of formula II $$\text{Hal-R}_1 \quad (II)$$

in which:

Hal represents a halogen atom, and $R_1$ represents a radical selected from:

a $C_1$ to $C_{18}$ linear or branched alkyl, optionally substituted by one or more halogen atoms, a $C_2$ to $C_{18}$ linear or branched alkenyl, optionally substituted by one or more halogen atoms, or an aralkyl, optionally substituted by one or more $C_1$ to $C_6$ alkoxy groups, or $COR_3$ or $CONHR_3$, wherein $R_3$ represents a radical selected from:

a $C_1$ to $C_{18}$ linear or branched alkyl, optionally substituted by one or more halogen atoms, a $C_2$ to $C_{18}$ linear or branched alkenyl, optionally substituted by one or more halogen atoms, an aralkyl, optionally substituted by one or more $C_1$ to $C_6$ alkoxy groups, an aralkenyl, optionally substituted by one or more $C_1$ to $C_6$ alkoxy groups and/or one or more OH groups, or an aryl radical, optionally substituted by one or more $C_1$ to $C_6$ alkoxy groups.

17. Method of preparing, according to claim 16, a derivative of resorcinol of formula (I) in which X represents SO or $SO_2$, wherein a compound of formula (I), in which X represents a sulphur atom, is oxidised by means of an aqueous solution of hydrogen peroxide.

* * * * *